(12) United States Patent
Russak

(10) Patent No.: US 9,026,481 B2
(45) Date of Patent: May 5, 2015

(54) REMOTE CHEMICAL ASSAY SYSTEM

(71) Applicant: Azure Vault Ltd., Ramat-Gan (IL)

(72) Inventor: Ze'ev Russak, Ramat Gan (IL)

(73) Assignee: Azure Vault Ltd., Netanya (IL)

( * ) Notice: Subject to any disclaimer, the term of this patent is extended or adjusted under 35 U.S.C. 154(b) by 0 days.

(21) Appl. No.: 14/146,020

(22) Filed: Jan. 2, 2014

(65) Prior Publication Data

US 2014/0113357 A1 Apr. 24, 2014

Related U.S. Application Data

(63) Continuation of application No. 13/115,185, filed on May 25, 2011, now Pat. No. 8,660,968.

(51) Int. Cl.
*G06F 15/18* (2006.01)
*C12Q 1/68* (2006.01)
*G06F 19/00* (2011.01)

(52) U.S. Cl.
CPC ......... *C12Q 1/686* (2013.01); *B01L 2300/0829* (2013.01); *G06F 19/702* (2013.01); *G06F 19/707* (2013.01)

(58) Field of Classification Search
USPC ...................................... 706/12, 45
See application file for complete search history.

(56) References Cited

U.S. PATENT DOCUMENTS

| | | | |
|---|---|---|---|
| 5,606,164 A | 2/1997 | Price et al. | |
| 6,289,328 B2 | 9/2001 | Shaffer | |
| 6,503,720 B2 | 1/2003 | Wittwer et al. | |
| 6,763,308 B2 | 7/2004 | Chu et al. | |
| 7,050,932 B2 | 5/2006 | Selby et al. | |
| 7,062,415 B2 | 6/2006 | Whitefield et al. | |
| 7,523,384 B2 | 4/2009 | Wold | |
| 7,542,959 B2 | 6/2009 | Barnhill et al. | |
| 7,664,328 B2 | 2/2010 | Wang et al. | |
| 2003/0041041 A1 | 2/2003 | Cristianini | |
| 2003/0144746 A1 | 7/2003 | Hsiung et al. | |
| 2006/0004753 A1 | 1/2006 | Coifman | |

(Continued)

FOREIGN PATENT DOCUMENTS

| | | | |
|---|---|---|---|
| WO | 0131579 A2 | 5/2001 | |
| WO | 03029924 A2 | 4/2003 | |

(Continued)

OTHER PUBLICATIONS

Zhang et al., Classification of Chemicals Based on Concentration-Dependent Toxicological Data Using ToxClust, 2009, Environ. Sci. Technol., pp. 1-7.*

(Continued)

*Primary Examiner* — David Vincent
(74) *Attorney, Agent, or Firm* — Michael A. Whittaker; Acuity Law Group, P.C.

(57) ABSTRACT

A portable device for remote chemical assay classification, comprising a computer processor, and an apparatus implemented on the computer processor, the apparatus comprising: an out-of-sample data receiver, configured to receive data defining an out-of-sample extension extracted on a remote computer from classifying test assays of a chemical reaction on the remote computer into at least two groups, and an assay classifier, in communication with the out-of-sample data receiver, configured to classify a new assay of the chemical reaction into one of the groups, using the data defining the out-of-sample extension.

15 Claims, 9 Drawing Sheets

(56) References Cited

U.S. PATENT DOCUMENTS

| | | |
|---|---|---|
| 2006/0014302 A1* | 1/2006 | Martinez et al. ............. 436/518 |
| 2006/0063156 A1 | 3/2006 | Willman et al. |
| 2006/0224330 A1 | 10/2006 | Kurnik |
| 2007/0021929 A1 | 1/2007 | Lemmo et al. |
| 2007/0055477 A1 | 3/2007 | Chickering et al. |
| 2007/0073489 A1 | 3/2007 | Kurnik et al. |
| 2007/0073490 A1 | 3/2007 | Kurnik |
| 2007/0124088 A1 | 5/2007 | Woo et al. |
| 2007/0129899 A1 | 6/2007 | Ward et al. |
| 2007/0148632 A1 | 6/2007 | Kurnik et al. |
| 2008/0167837 A1 | 7/2008 | Basak et al. |
| 2008/0177478 A1 | 7/2008 | Hlavacek et al. |
| 2008/0234977 A1 | 9/2008 | Aggarwal et al. |
| 2008/0261220 A1* | 10/2008 | Cracauer et al. ............... 435/6 |
| 2009/0119020 A1 | 5/2009 | Kurnik et al. |
| 2009/0192754 A1 | 7/2009 | Balog et al. |
| 2010/0063835 A1 | 3/2010 | Kenedy et al. |
| 2010/0293124 A1 | 11/2010 | Berger et al. |
| 2011/0251075 A1* | 10/2011 | McDevitt et al. ................ 506/7 |
| 2012/0284049 A1* | 11/2012 | Baym et al. ...................... 705/3 |

FOREIGN PATENT DOCUMENTS

| | | |
|---|---|---|
| WO | 2006023744 A2 | 3/2006 |
| WO | 2007113622 A2 | 10/2007 |
| WO | 2008039918 A2 | 4/2008 |

OTHER PUBLICATIONS

Li et al., Supervised Learning on Local Tangent Space. Advances in Neural Networks—ISNN 2005;3496:546-551.

Platt, FastMap, MetricMap, and Landmark MDS are all Nystrom Algorithms. Microsoft Research Technical Report MSR-TR-2004-26, Sep. 28, 2004:1-15.

* cited by examiner

REMOTE CHEMICAL ASSAY SYSTEM

FIELD AND BACKGROUND OF THE INVENTION

The present invention relates to analyzing chemical reactions and, more to particularly, but not exclusively to systems and methods for remote classification of chemical reaction assays.

Traditionally, the classification of the assays is based on manual examination by an expert in the field. The expert manually examines hundreds or thousands of samples, say thousands of graphs derived from Quantitative-Fluorescent Polymerase Chain Reaction (QF-PCR) based assays.

The expert manually detects certain features in the samples, and classifies each sample into one of two or more groups of chemical reactions (say as negative or positive, with respect to presence of a certain genetic mutation).

Some currently used methods provide for semi-automatic classification of chemical reaction assays.

For example, PCT Patent Application No.: PCT/IB2006/051025, filed on Apr. 4, 2006, to Tichopad et al., entitled "Assessment of Reaction Kinetics Compatibility between Polymerase Chain Reactions", describes the usage of a large training set, to statistically compare properties of chemical assays.

Similarly, Wold et al, describe in a 1977 article, entitled "SIMCA: A method for analyzing chemical data in terms of similarity and analogy", in Kowalski, B. R., ed., Chemometrics Theory and Application, American Chemical Society Symposium Series 52, Wash., D. C., American Chemical Society, pp. 243-282, a similarity analysis method. The Wold method requires availability of a large amount of test sample data, with a multitude of attributes and class memberships.

However, the above described methods still rely on a training set built manually, by the expert. In order to build the training set, the expert has to manually examine hundreds or thousands of samples, and classify each sample into one of two or more groups of chemical reactions.

Some currently used methods are based on automatic classification of samples. For example, some of the currently used methods use SVM (Support Vector Machine), to identify patterns in biological systems.

Support Vector Machine (SVM) is a set of related supervised learning methods that analyze data and recognize patterns. Supervised learning methods are widely used for classification and regression analysis.

Intuitively, an SVM built model is a representation of the samples as points in a space, mapped so that the examples of the separate categories are divided by a clear gap.

Typically, a preliminary step in the classification of chemical reaction assays involves feature extraction from a large number of test assays.

In one example, the feature extraction includes, among others, extraction of parameters from a QF-PCR chemical reaction graph of each of the test assays, say extraction of coordinate values of elbow points that need to be detected on the QF-PCR chemical reaction graph.

The parameters may include, but are not limited to parameters such as Fluorescence Intensity (FI) value of the one or more elbow points detected on the QF-PCR chemical reaction graph, a time of each of the elbow points, Fluorescence Intensity (FI) values at certain points of the QF-PCR chemical reaction graph, etc.

The extracted parameters are then used to classify the test assays, say through SVM or another supervised learning method, as known in the art.

SUMMARY OF THE INVENTION

According to one aspect of the present invention, there is provided a portable device for remote chemical assay classification, comprising a computer processor and an apparatus implemented on the computer processor. The apparatus comprises: an out-of-sample data receiver, configured to receive data defining an out-of-sample extension extracted on a remote computer from classifying test assays of a chemical reaction on the remote computer into at least two groups, and a new assay classifier, in communication with the out-of-sample data receiver, configured to classify a new assay of the chemical reaction into one of the groups, using the data defining the out-of-sample extension.

According to a second aspect of the present invention, there is provided an apparatus for remote chemical assay classification, the apparatus comprising: a test assay classifier, configured to classify a plurality of test assays of a chemical reaction into at least two groups, an extension extractor, in communication with the test assay classifier, configured to extract an out-of-sample extension from the classifying of the test assays, and a data packager, in communication with the extension extractor, configured to package data defining the extracted out-of-sample extension, for delivery to a remote computer used for classifying a new assay of the chemical reaction into one of the groups, using the data defining the out-of-sample extension.

According to a third aspect of the present invention, there is provided an apparatus for remote chemical assay classification, the apparatus comprising: an out-of-sample data receiver, configured to receive data defining an out-of-sample extension extracted on a remote computer from classifying test assays of a chemical reaction on the remote computer into at least two groups, and a new assay classifier, in communication with the out-of-sample data receiver, configured to classify a new assay of the chemical reaction into one of the groups, using the data defining the out-of-sample extension.

According to a fourth aspect of the present invention, there is provided a computer implemented method for remote chemical assay classification, the method comprising steps a computer is programmed to perform, the steps comprising: classifying a plurality of test assays of a chemical reaction into at least two groups, extracting an out-of-sample extension from the classifying, and packaging data defining the extracted out-of-sample extension, for delivery to a remote computer used for classifying a new assay of the chemical reaction into one of the groups, using the data defining the out-of-sample extension.

According to a fifth aspect of the present invention, there is provided a computer implemented method for remote chemical assay classification, the method comprising steps a computer is programmed to perform, the steps comprising: receiving data defining an out-of-sample extension extracted on a remote computer from classifying test assays of a chemical reaction on the remote computer into at least two groups, and classifying a new assay of the chemical reaction into one of the groups, using the data defining the out-of-sample extension.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

Moreover, according to actual instrumentation and equipment of preferred embodiments of the method and system of the present invention, several selected steps could be implemented by hardware or by software on any operating system of any firmware or a combination thereof.

For example, as hardware, selected steps of the invention could be implemented as a chip or a circuit. As software, selected steps of the invention could to be implemented as a plurality of software instructions being executed by a computer using any suitable operating system.

In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings.

With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention.

Figure 1:
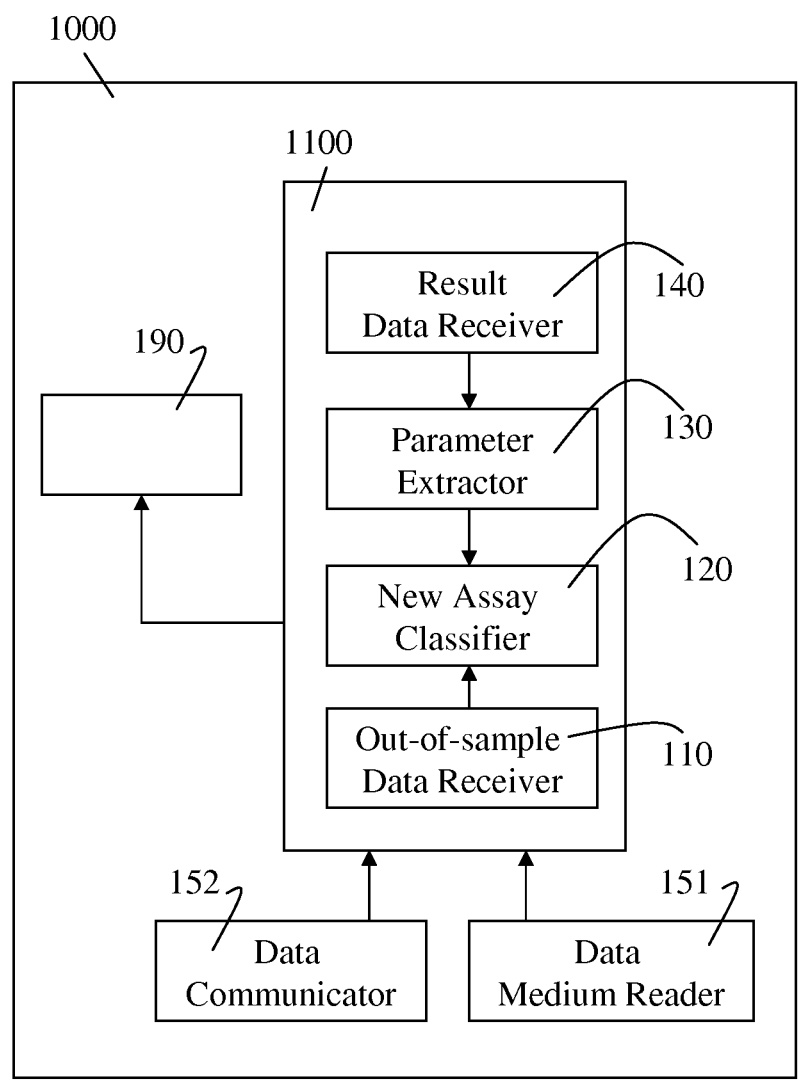

The description taken with the drawings making apparent to those skilled in the art how the several forms of the invention may be embodied in practice.

In the drawings:

FIG. 1 is a simplified block diagram schematically illustrating a first portable device for remote chemical assay classification, according to an exemplary embodiment of the present invention.

Figure 2:
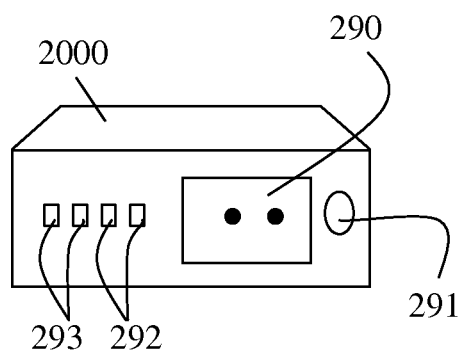

FIG. 2 is a simplified block diagram schematically illustrating a second portable device for remote chemical assay classification, according to an exemplary embodiment of the present invention.

Figure 3:
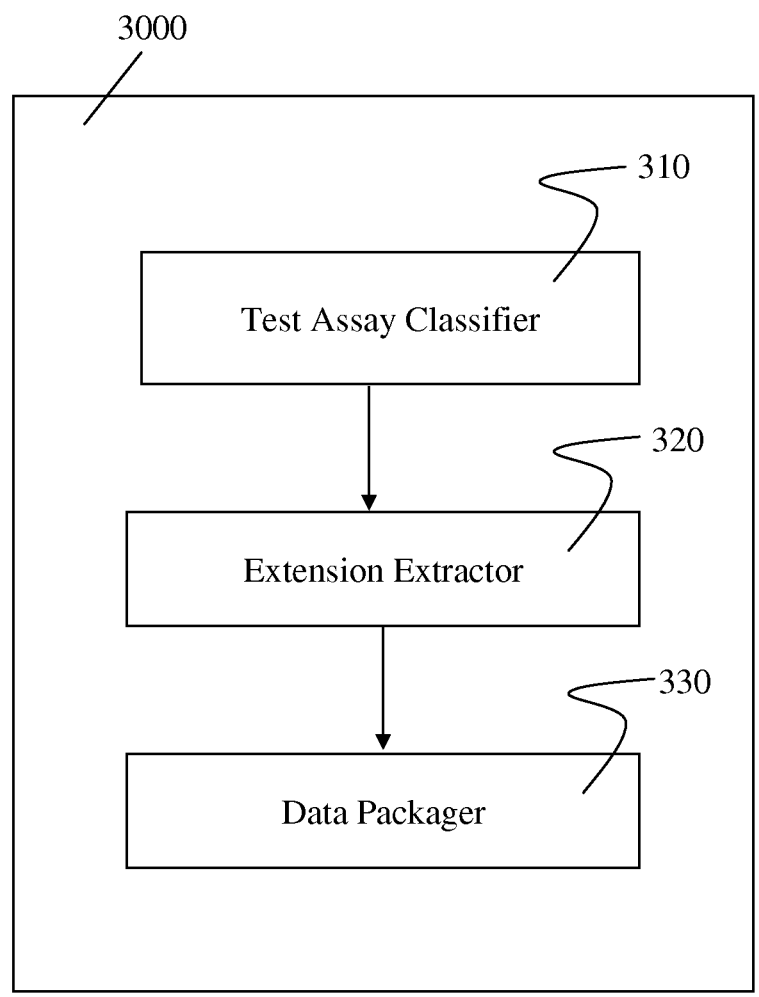

FIG. 3 is a simplified block diagram schematically illustrating a first apparatus for remote chemical assay classification, according to an exemplary embodiment of the present invention.

Figure 4:
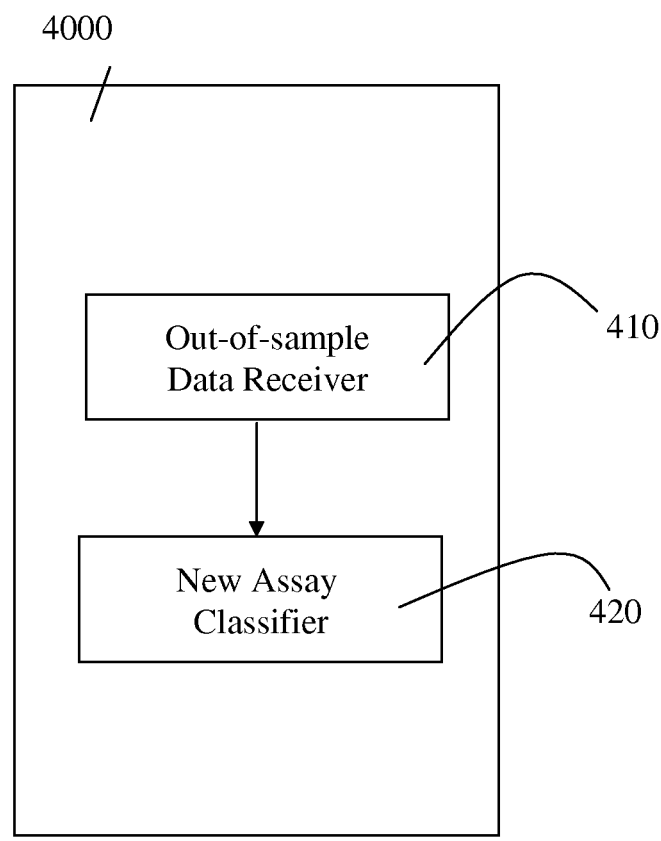

FIG. 4 is a simplified block diagram schematically illustrating a second apparatus for remote chemical assay classification, according to an exemplary embodiment of the present invention.

Figure 5:
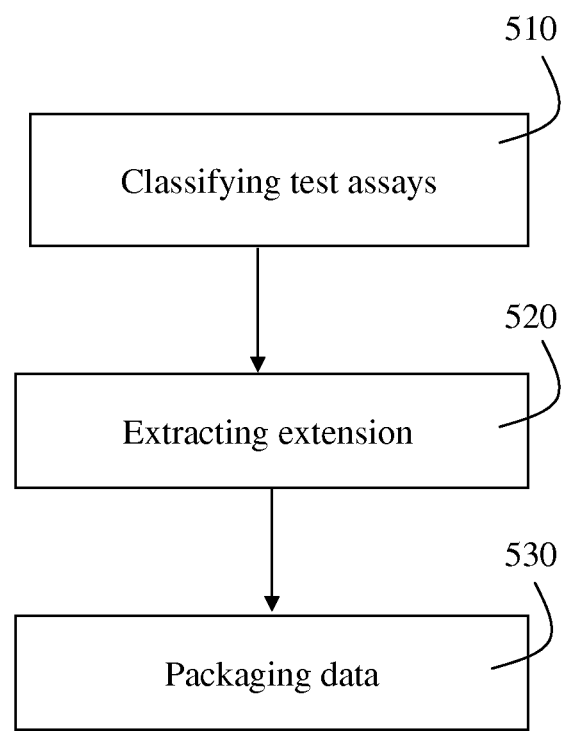

FIG. 5 is a simplified flowchart illustrating a first method for remote chemical assay classification, according to an exemplary embodiment of the present invention.

Figure 6:
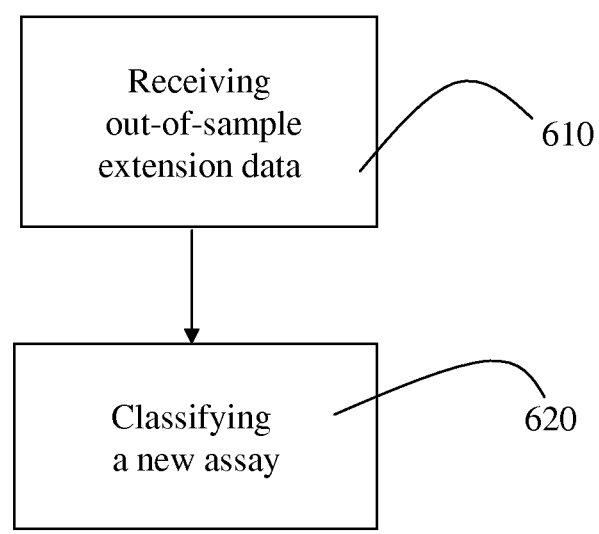

FIG. 6 is a simplified flowchart illustrating a second method for remote chemical assay classification, according to an exemplary embodiment of the present invention.

Figure 7A:
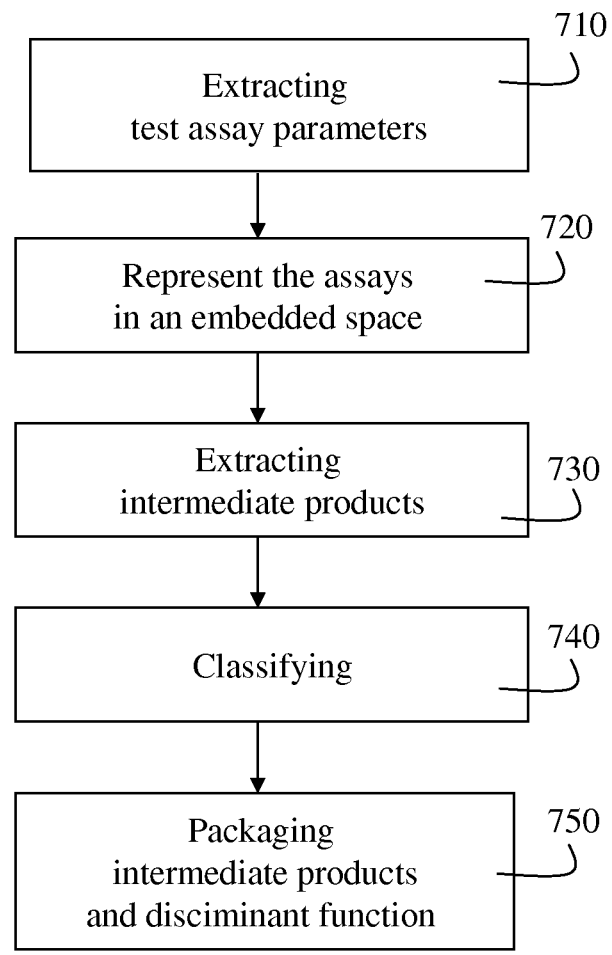

FIG. 7A is a simplified flowchart illustrating a third method for remote chemical assay classification, according to an exemplary embodiment of the present invention.

Figure 7B:
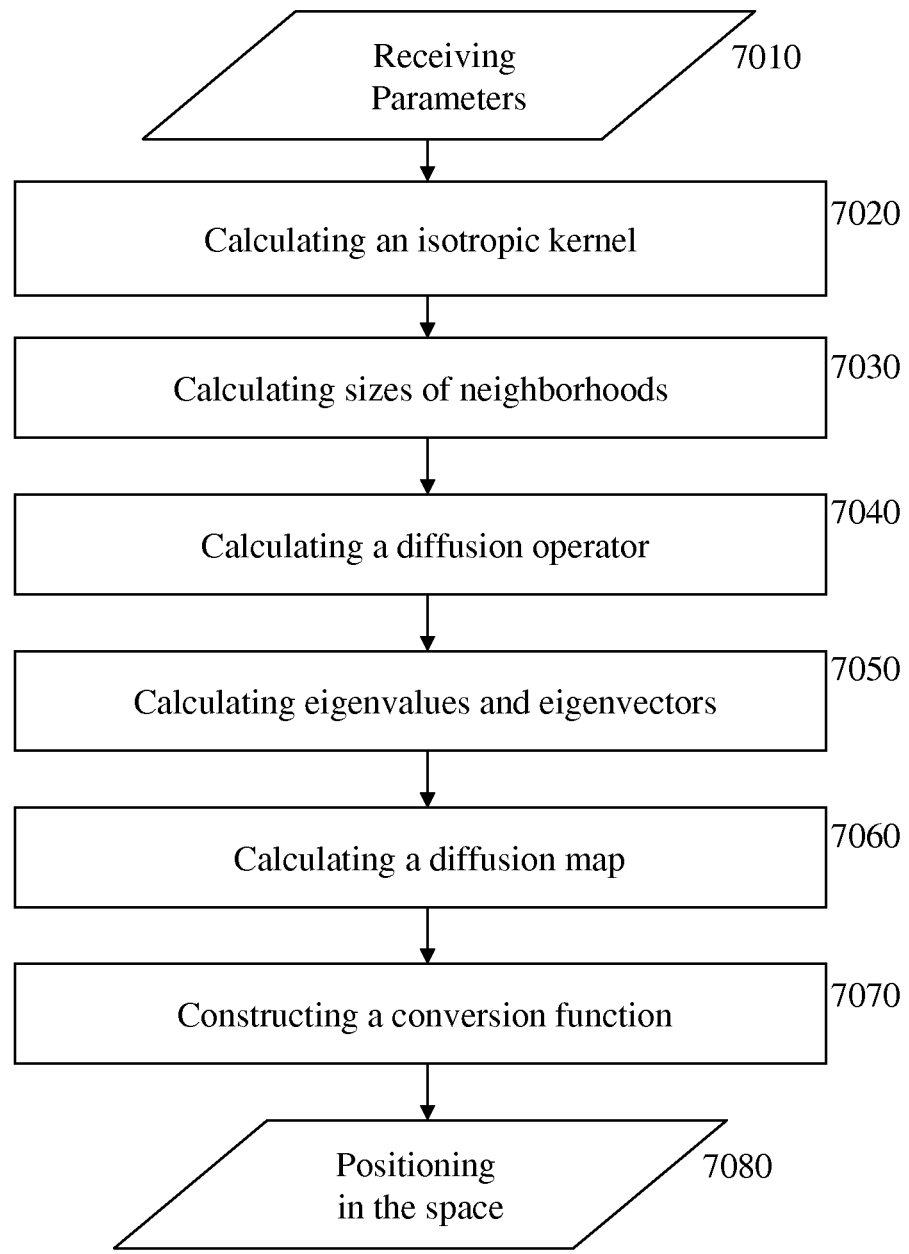

FIG. 7B is a simplified flowchart illustrating a fourth method for remote chemical assay classification, according to an exemplary embodiment of the present invention.

Figure 8:
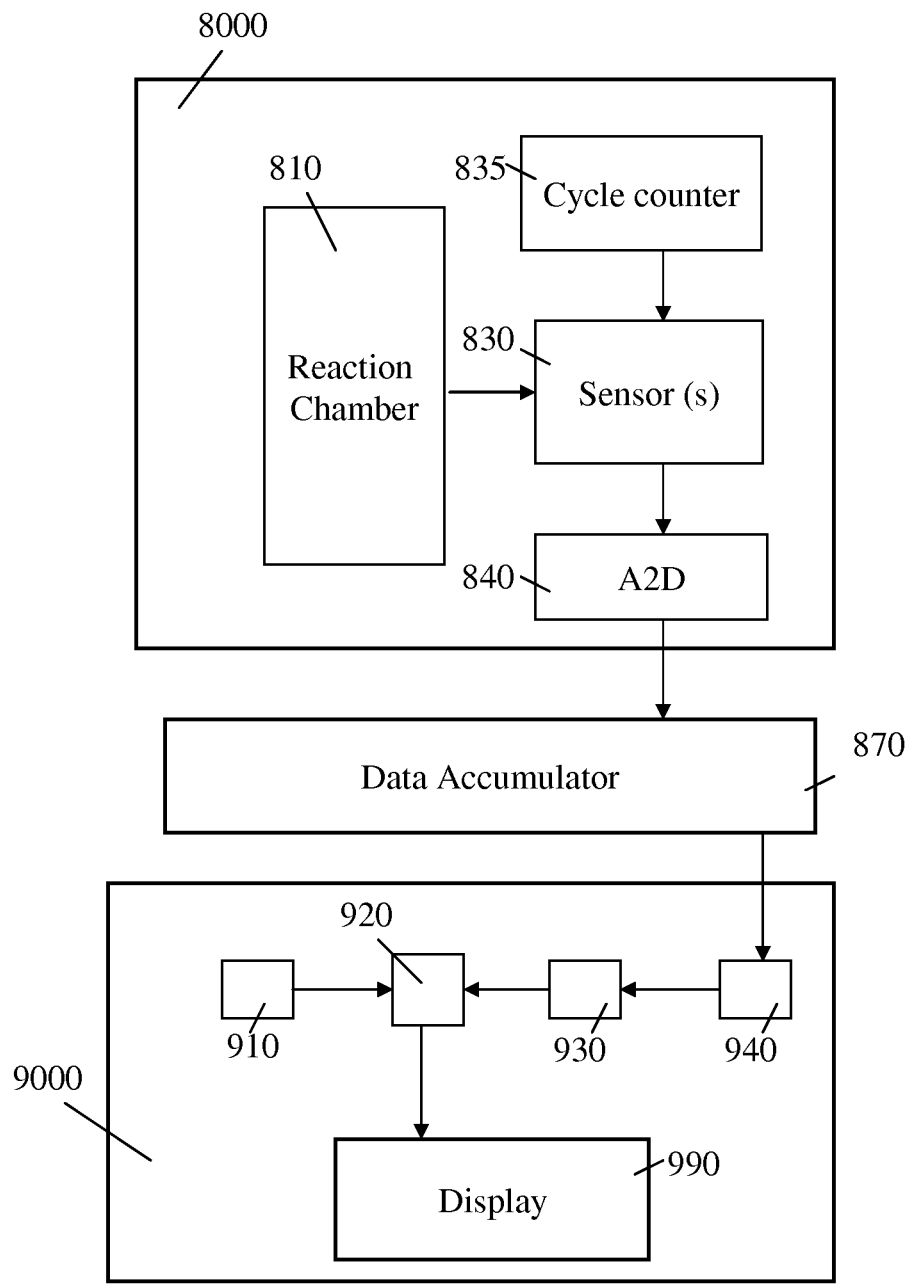

FIG. 8 is a block diagram schematically illustrating a system for remote chemical assay classification, according to an exemplary embodiment of the present invention.

DESCRIPTION OF THE PREFERRED EMBODIMENTS

The present embodiments comprise a portable device, an apparatus, and a method, for remote chemical assay classification.

According to an exemplary embodiment of the present invention, a central computer is used for classifying a large number of chemical reaction test assays into two or more groups (say positive assays vs. negative assays). Consequently, there is yielded a classification model usable for classifying new assays of the chemical reaction.

In one example, the central computer is a computer used by a central laboratory, or a computer used by a party which provides classification services to several laboratories in a SaaS (Software as a Service) mode, as describe in further detail hereinbelow.

The classification of the test assays on the central computer may include a preliminary step of feature extraction.

The feature extraction step involves extracting certain parameters from result data of each one of a large number of test assays carried out by a laboratory.

In one example, the feature extraction step involves extracting certain parameters from Quantitative Fluorescent (QF) values measured during a Polymerase Chain Reaction (PCR) used for each of the test assays of the example.

In the example, the feature extraction may include, among others, extraction of parameters from a graph which depicts the Quantitative Fluorescent Polymerase Chain Reaction QF-PCR chemical reaction values measured during the chemical reaction.

Example parameters include, but are not limited to coordinate values (such as time and amplitude) of elbow points that need to be detected on the QF-PCR chemical reaction graph, amounts of products yielded in the chemical reaction, etc.

Then, each of the test assays is represented by a point in a mathematical space (say a Euclidian space) in which each dimension corresponds to one of test assay's parameters. The position of each point depends on the values of the parameters extracted from the test assay represented by the point.

Next, the points are subjected to computationally heavy classification techniques.

The classification techniques applied on the points that represent the large number of test assays, require extensive computational resources, typically found on strong computer servers used by big laboratories and academic institutions.

The classification techniques may include one or more learning techniques, such as SVM (Support Vector Machine), K-Nearest Neighbor, etc., as known in the art.

An accurate classification of the test assays is likely to involve characterizing each of the test assays by a multitude of extracted parameters, thus increasing the mathematical space's dimensionality. Further, some learning techniques, such as SVM, involve further increase in the number of dimensions, as known in the art.

The more dimensions the mathematical space has, the more computationally heavy the classification techniques become.

In order to decrease the number of dimensions, the classification techniques may further involve dimensionality reduction techniques such as Diffusion Mapping (introduced in very recent years), Kernel PCA, Laplacian Eigen-mapping, Isomapping, MVU (Maximum Variance Unfolding), etc.

The dimensionality reduction techniques reduce the number of dimensions in the mathematical space, and improve separation between groups of test assays of different qualities (say positive vs. negative).

Consequently, the dimensionality reduction techniques provide for more accurate classification of the test assays, when subjected to SVM or an alternative learning technique.

However, the dimensionality reduction techniques further add to the classification's computational complexity.

In one example, a diffusion mapping technique converts the mathematical space into a dimensionally reduced space, which enhances proximity among points that represent assays of similar qualities. The dimensionally reduced space is also referred to hereinbelow, as an embedded space.

However, diffusion mapping is also a computationally heavy technique, which consumes large amounts of random access memory and processing power.

Upon applying classification techniques such as SVM on the points of the embedded space, there is yielded a classification model in which one or more lines separate the embedded space into the groups.

SVM yields a discriminant function, which indicates for each of the points (and hence for the test assay represented by the point), the point's belonging to one of the groups, based on location of the point in the embedded space or on values of the parameters extracted for the test assay represented by the point.

The embedded space depends on relations among the test assay's results. That is to say that the points are positioned in the embedded space according to the relations between the points, as well as the values of the parameters extracted from each of the chemical reaction assays, as described in further detail hereinbelow.

When a new assays needs to be classified, a completely accurate classification of the new assay requires a computationally heavy re-calculation of the whole embedded space, using results of both the test assays and the new assay.

According to an exemplary embodiment of the present invention, an out-of-sample extension is extracted from the classification of the test assays, on the central server.

Each dimensionality reduction technique may have one (or more) out-of-sample extensions, as known in the art and described in further detail hereinbelow.

The out-of-sample extension is a method for classifying a new assay into one to of the groups (say the negative and positive groups) resultant upon the classification of the test assays.

The out-of-sample extension classifies the new assay without a complete re-calculating of the embedded space, say using intermediate products of the classification of the test assay, as described in further detail hereinbelow.

While, the out-of-sample extension is computationally simpler than the techniques used for classifying the test assays (as the extension avoids the complete recalculation of the embedded space), the out-of-sample extension involves a tolerable loss in accuracy of classification.

Next, data which defines the extension, is packaged (say in a file of a specific format), and sent to a remote portable device used for classifying a new assay of the chemical reaction, say in a field laboratory distant from the central computer.

In one example, the data, which defines the extension, consists of intermediate products of the diffusion mapping technique and a discriminant function of an SVM technique applied on the embedded space, for classifying the test assays, as described in further detail hereinbelow.

The remote portable device may be a compact, light weight device, dedicated for classification of new assays, with computational resources that are inferior to the central computer's computational resources, such as a slower processor, a smaller data storage capacity, different software, etc., as described in further detail hereinbelow.

The remote portable device uses the data which defines the out-of-sample extension, to classify a new assay into one of the groups, using the computationally simpler out-of-sample extension, thus providing for a remote chemical assay classification, as described in further detail hereinbelow.

The principles and operation of a according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1, which is a simplified block diagram schematically illustrating a first portable device for remote chemical assay classification, according to an exemplary embodiment of the present invention.

A first portable device 1000, for remote chemical assay classification, according to an exemplary embodiment of the present invention, includes a computer processor 1100, and an apparatus implemented on the computer processor 1100, as a computer program.

The apparatus implemented on the computer processor 1100, includes an out-of-sample data receiver 110.

The out-of-sample data receiver 110 receives data which defines an out-of-sample extension, as described in further detail hereinbelow.

The out-of-sample extension is extracted on a remote computer (say on a server used by a central laboratory or a company which provides classification services to laboratories), and sent to the portable device 1000, as described in further detail hereinbelow.

The out-of-sample extension is extracted from classifying test assays of a chemical reaction on the remote computer into at least two groups, say using learning techniques and dimensionality reduction techniques, as described in further detail hereinbelow.

Optionally, the classification of the test assays on the remote computer is based on a non-linear technique such as diffusion mapping. The data which defines the extracted out-of-sample extension may include intermediary products of the non-linear technique, say selected matrices, as described in further detail hereinbelow.

Optionally, the classification of the test assays on the remote computer is based on diffusion mapping and SVM, and the data which defines the extension, consists of intermediate products of the diffusion mapping technique and an SVM discriminant function, as described in further detail hereinbelow.

The apparatus further includes a new assay classifier 120, in communication with the out-of-sample data receiver 110.

The new assay classifier 120 classifies a new assay of the chemical reaction into one of the groups that the test assays are classified into, using the data which defines the out-of-sample extension, as described in further detail hereinbelow.

Optionally, the apparatus further includes a parameter extractor 130, in communication with the new assay classifier 110.

The parameter extractor 130 extracts one or more parameters from result data of the new assay, and the new assay classifier 120 uses the extracted parameters, for classifying the new assay, as described in further detail hereinbelow.

Optionally, the apparatus further includes a result data receiver 140, in communication with the parameter extractor 130.

The result data receiver 140 receives result data of the new assay, and the new assay classifier 120 uses the received result data, or parameters extracted from the received result data (say by the parameter extractor 130), for classifying the new assay, as described in further detail hereinbelow.

Optionally, the portable device 1000 further includes a data medium reader 151, in communication with the computer processor 1100 and with the new assay classifier 110 implemented on the computer processor 1100.

Optionally, the data medium reader 151 reads the data which defines the out-of-sample extension, from a computer readable medium (such as a USB-Memory, an SD (Secure Digital) card, a smart card, etc), for the out-of-sample data receiver 110.

Optionally, the result receiver 140 may use the data medium reader 151 or another data medium reader installed in the portable device 1000, to read result data of the new assay from a computer readable medium.

The new assay classifier 120 uses the read result data, or parameters extracted form the read result data (say by the parameter extractor 130), and the data which defines the out-of-sample extension, for classifying the new assay, as described in further detail hereinbelow.

Optionally, the portable device 1000 further includes a data communicator 152 (say a modem or a computer network card, as known in the art), in communication with the computer processor 1100.

Optionally, the data communicator 152 communicates with the remote computer, for receiving the data which defines the out-of-sample extension, say through a cellular network, through the internet, or through another communication channel, as known in the art.

Optionally, the data communicator 152, or another data communicator, installed in the portable device 1000, communicates with a computer coupled to a chemical reaction apparatus in which the new assay is carried out.

The data communicator 152 (or the other data communicator) communicates with the computer coupled to the chemical reaction apparatus, for receiving result data of the new assay from the coupled computer. The new assay classifier 120 uses the result data or parameters extracted from the result data (say by the parameter extractor 130), for classifying the new assay, as described in further detail hereinbelow.

The portable device 1000 may further include a display 190, such as a small LCD (Liquid Crystal Display) screen or a set of small LED (Light Emitting Diode) lights, in communication with the computer processor 1100.

The display may be used to convey messages to a user of the portable device 1000.

For example, upon successful classification of the new assay, the result of the classification of the new assay may be conveyed to the user of the portable device 1000, say by turning on one of the LED lights (say a green light), or through a message presented on the small LCD screen (say a 'Positive Assay' message).

Optionally, the apparatus implemented on the computer processor 1100, further includes a classification data writer, in communication with the new assay classifier 120, say a DVD Writer, or a CD Writer, as known in the art.

The classification data writer may be used by the new assay classifier 120, for writing the results of the classification of new assay into a computer readable medium, such as CD-ROM, an SD Memory Card, a USB-Memory, etc., as known in the art.

Reference is now made to FIG. 2, which is a simplified block diagram schematically illustrating a second portable device for remote chemical assay classification, according to an exemplary embodiment of the present invention.

A second exemplary portable device 2000, for remote chemical assay classification, includes the apparatus implemented on the computer processor 1100 of device 1000.

Optionally, the second apparatus 2000 further includes two LED lights 290 (say a green light—for positively classified assays and a red light—for negatively classified assays). The LED lights 260 may be used to convey results of classification of a new assay, to a user of the second apparatus 2000, say using the new assay classifier 120, as described in further detail hereinabove.

The second exemplary portable device 2000 may further include an on/off switch 291, for turning the portable device 2000 on or off, as known in the art.

The second device 2000 may further include one or more control buttons 292, say for switching between reading the data which defines the out-of-sample extension and reading result data of the new assay, as described in further detail hereinabove.

The second device 2000 may further include one or more sockets 293.

Optionally, one or more of the sockets are used to write results of a new assay's classification by the new assay classifier 120, onto a computer readable medium, say onto an SD-Memory Card, a USB-Memory card, etc., as described in further detail hereinabove.

Optionally, one or more of the sockets may be used for inserting a computer readable medium (say a USB-Memory or an SD-Memory Card), which carries the data which defines the out-of-sample extension, for reading by the data medium reader 151, as described in further detail hereinabove.

The second portable device 2000 may be a compact, light weight device, dedicated for classification of new assays, with relatively limited computational resources, such as a slow processor, a minimal data storage capacity, etc.

Consequently, the portable device 2000 may prove very helpful, for small (and even field) laboratories that lack a computer strong enough for carrying out the computationally heavy classification techniques, as described in further detail hereinabove.

Reference is now made to FIG. 3, which is a simplified block diagram schematically illustrating a first apparatus for remote chemical assay classification, according to an exemplary embodiment of the present invention.

An exemplary apparatus 3000 may be implemented as a computer program, as hardware, as a combination of a computer program and hardware, etc.

Optionally, the apparatus 3000 is implemented as a computer server application in remote communication with one or more dedicated client programs installed on remote computers (say on remote laboratory computers, as described in further detail hereinbelow).

The apparatus 3000 includes a test assay classifier 310.

The test assay classifier 310 classifies a plurality of test assays of a chemical reaction into at least two groups, say into a group of negative assays and a group of positive assays.

The test assay classifier may classify the test assays using learning techniques and dimensionality reduction techniques, as described in further detail hereinbelow.

The apparatus 3000 further includes an extension extractor 320, in communication with the test assay classifier 310.

The extension extractor 320 extract an out-of-sample extension from the classifying of the test assays, as described in further detail hereinbelow.

The apparatus 3000 further includes a data packager 330, in communication with the extension extractor 320.

The data packager 330 packages data which defines the extracted out-of-sample extension, for delivery to a remote computer used for classifying a new assay of the chemical reaction into one of the groups.

Optionally, the remote computer is coupled to a chemical reaction apparatus in which the new assay is carried out, as described in further detail hereinbelow.

Optionally, the test assay classifier 310 classifies the test assays using a non-linear technique such as diffusion mapping. The packaged data may include intermediary products of the non-linear technique, say selected matrices, as described in further detail hereinbelow.

Optionally, the test assay classifier 310 classifies the test assays, using diffusion mapping and SVM. The data which defines the extension may consist of intermediate products (say matrices) of the diffusion mapping technique and an SVM discriminant function, as described in further detail hereinbelow.

In one example, the data packager 330 packages the data in a file of a specific format, say a format which complies with an agreed upon standard, say an industry standard which may be established.

Optionally, the apparatus 3000 further includes a data communicator (say a modem or a computer network card), in communication with the data packager 330.

The data communicator communicates the packaged data to the remote computer.

Optionally, the apparatus 3000 further includes a data writer, in communication with the data packager 330.

The data writer writes the packaged data onto a portable medium readable by the remote computer, say onto a SD memory card, a USB memory, a smart card, etc.

The portable medium is sent to a user of the remote computer, who inserts the medium into a socket on the remote computer.

The remote computer reads the packaged data, and uses the out-of-sample extension defined by the read data, for classifying the new assay of the chemical reaction, as described in further detail hereinbelow.

In one example, the apparatus 3000 further includes a parameter extractor, in communication with the test assay classifier 310.

The parameter extractor extracts one or more parameters from result data of the test assays, and the test assay classifier 310 uses the extracted parameters, for classifying the test assays, as described in further detail hereinbelow.

Optionally, the apparatus 3000 further includes a test data receiver, say a test data receiver in communication with the parameter extractor.

The test data receiver receives result data of the test assays, and the test assay classifier 310 uses the received result data, or parameters extracted from the received result data (say by the parameter extractor), for classifying the test assay, as described in further detail hereinbelow.

Reference is now made to FIG. 4, which is a simplified block diagram schematically illustrating a second apparatus for remote chemical assay classification, according to an exemplary embodiment of the present invention.

An exemplary apparatus 4000, for remote chemical assay classification, according to an exemplary embodiment of the present invention, may be implemented as a computer program, as hardware, as a combination of a computer program and hardware, etc.

Apparatus 4000 includes an out-of-sample data receiver 410.

The out-of-sample data receiver 410 receives data which defines an out-of-sample extension, as described in further detail hereinbelow.

The out-of-sample extension is extracted on a remote computer (say on a server used by a central laboratory or a company which provides classification services to laboratories), as described in further detail hereinbelow.

The out-of-sample extension is extracted from classifying test assays of a chemical reaction on the remote computer into at least two groups, say using learning techniques and dimensionality reduction techniques, as described in further detail hereinbelow.

Optionally, the classification of the test assays on the remote computer is based on a non-linear technique such as diffusion mapping. The data which defines the extracted out-of-sample extension, may include intermediary products of the non-linear technique, say selected matrices, as described in further detail hereinbelow.

Optionally, the classification of the test assays on the remote computer is based on diffusion mapping and SVM. The data which defines the extension, may consist of intermediate products (say matrices) of the diffusion mapping technique, and an SVM discriminant function, as described in further detail hereinbelow.

The apparatus 4000 further includes a new assay classifier 420, in communication with the out-of-sample data receiver 410.

The new assay classifier 420 classifies a new assay of the chemical reaction into one of the groups that the test assays are classified into, using the data which defines the out-of-sample extension.

Optionally, the apparatus further includes a parameter extractor, in communication with the new assay classifier 420.

The parameter extractor extracts one or more parameters from result data of the new assay, and the new assay classifier 420 uses the extracted parameters, for classifying the new assay, as described in further detail hereinbelow.

Optionally, the apparatus 4000 further includes a result data receiver, in communication with the parameter extractor.

The result data receiver receives result data of the new assay, and the new assay classifier 420 uses the received result data, or parameters extracted from the received result data (say by the parameter extractor), for classifying the new assay, as described in further detail hereinbelow.

Optionally, the apparatus 4000 further includes a data communicator (say a modem or a computer network card, as known in the art), in communication with the out-of-sample data receiver 410.

The data communicator communicates with the remote computer, for receiving the data which defines the out-of-sample extension, say through a cellular network, through the internet, or through another communication channel, as known in the art.

Optionally, the data communicator further communicates with a computer coupled to a chemical reaction apparatus in which the new assay is carried out, for receiving result data of the new assay from the coupled computer.

The new assay classifier 420 uses the result data or parameters extracted from the result data (say by the parameter extractor), for classifying the new assay, as described in further detail hereinbelow.

Optionally, the apparatus 4000 itself is coupled to the chemical reaction apparatus in which the new assay is carried out, as described in further detail hereinbelow.

For example, the apparatus 4000 may be implemented on a chip installed on the chemical reaction apparatus, say as a part of a controller connected to sensors inside a chemical reaction chamber, which forms a part of the chemical reaction apparatus, as described in further detail hereinbelow.

Reference is now made to FIG. 5, which is a simplified flowchart illustrating a first method for remote chemical assay classification, according to an exemplary embodiment of the present invention.

A first exemplary method, according to an exemplary embodiment of the present invention may be implemented using electric circuits, computer instructions, etc.

The first exemplary method includes steps that a computer is programmed to perform.

Optionally, the first exemplary method is implemented on a computer server in remote communication with one or more dedicated client programs installed on remote computers (say on remote laboratory computers), as described in further detail hereinbelow.

In the first exemplary method, a plurality of test assays of a chemical reaction are classified 510 into two or more groups, say into a group of negative assays and a group of positive assays.

Optionally, the test assays are classified by the test assay classifier 310, as described in further detail hereinabove.

Optionally, the test assays are classified 510, using learning techniques and dimensionality reduction techniques, as described in further detail hereinbelow.

Further in the first exemplary method, there is extracted 520 an out-of-sample extension, from the classifying of the test assays, say using the extension extractor 320, as described in further detail hereinbelow.

Next, data which defines the extracted out-of-sample extension, is packaged 530 for delivery to a remote computer used for classifying a new assay of the chemical reaction into one of the groups.

Optionally, the data which defines the extension is packaged by the data packager 330, as described in further detail hereinabove.

Optionally, the remote computer is coupled to a chemical reaction apparatus in which the new assay is carried out, as described in further detail hereinbelow.

Optionally, the test assays are classified 510, using a non-linear technique such as diffusion mapping. The packaged data may include intermediary products of the non-linear technique, say selected matrices created in an intermediate step of the non-linear technique, as described in further detail hereinbelow.

Optionally, the classification of the test assays is based on diffusion mapping and SVM. The data which defines the extension, may consist of intermediate products (say matrices) of the diffusion mapping technique and an SVM discriminant function, as described in further detail hereinbelow.

In one example, the data which defines the out-of-sample extension is packaged 530 in a file of a specific format, say a format which complies with an agreed upon standard.

Optionally, the packaged 530 data is communicated to the remote computer, using a modem or a computer network card, as described in further detail hereinabove.

Optionally, the packaged 530 data is written onto a portable medium readable by the remote computer, say onto a SD memory card, a USB memory, a smart card, etc, as described in further detail hereinabove.

The portable medium may be sent to a user of the remote computer, who inserts the medium into a socket on the remote computer. The remote computer reads the packaged 530 data, and uses the extracted out-of-sample extension defined by the read data, for classifying the new assay of the chemical reaction, as described in further detail hereinbelow.

In one example, the first exemplary method further includes extracting one or more parameters from result data of the test assays, as described in further detail hereinabove.

The extracted parameters may be used for classifying 510 the test assay, as described in further detail hereinbelow Optionally, the first exemplary method further includes receiving result data of the test assays, as described in further detail hereinabove.

Reference is now made to FIG. 6, which is a simplified flowchart illustrating a second method for remote chemical assay classification, according to an exemplary embodiment of the present invention.

A second exemplary method, according to an exemplary embodiment of the present invention may be implemented using electric circuits, computer instructions, etc.

The second exemplary method includes steps that a computer is programmed to perform.

Optionally, the second method is implemented on apparatus 4000, on the apparatus implemented on the computer processor 1100 of the portable device of FIG. 1, or on a computer processor of the portable device of FIG. 2, as described in further detail hereinabove. The second exemplary method includes steps that the computer server is programmed to perform.

The second exemplary method includes a step of receiving 610 data which defines an out-of-sample extension, say using the out-of-sample data receiver 410, as described in further detail hereinabove.

The out-of-sample extension is extracted on a remote computer (say on a server used by a central laboratory or a company which provides classification services to laboratories), as described in further detail hereinabove.

The out-of-sample extension is extracted from classifying test assays of a chemical reaction on the remote computer into at least two groups, say using learning techniques and dimensionality reduction techniques, as described in further detail hereinbelow.

Optionally, the classification of the test assays on the remote computer is based on a non-linear technique such as diffusion mapping. The data which defines the extracted out-of-sample extension may include intermediary products of the non-linear technique (say matrices calculated during the diffusion mapping), as described in further detail hereinbelow.

Optionally, the classification of the test assays on the remote computer is based on diffusion mapping and SVM, and the data which defines the extension, consists of intermediate products (say matrices) of the diffusion mapping technique and an SVM discriminant function, as described in further detail hereinbelow.

The second exemplary method further includes a step of classifying 620 a new assay of the chemical reaction into one of the groups that the test assays are classified into, using the data which defines the out-of-sample extension.

Optionally, the new assay is classified 620 using the new assay classifier 420 of apparatus 4000, as described in further detail hereinabove.

Optionally, the second exemplary method further includes extracting one or more parameters from result data of the new assay, say using the parameter extractor of apparatus 4000, as described in further detail hereinabove. The extracted parameters are used, for classifying 620 the new assay, as described in further detail hereinbelow.

Optionally, the second exemplary method further includes receiving result data of the new assay, and using the received result data, or parameters extracted from the received result data (say by the parameter extractor), for classifying 620 the new assay, as described in further detail hereinbelow.

Optionally, the second exemplary method further includes communicating with the remote computer, for receiving the data which defines the out-of-sample extension, as described in further detail hereinabove.

The remote computer may be communicated with, through a cellular network, through the internet, or through another communication channel, say using a modem or a computer network card, as described in further detail hereinabove.

Optionally, the second exemplary method further includes communicating with a computer coupled to a chemical reaction apparatus in which the new assay is carried out, for receiving result data of the new assay from the coupled computer.

The result data or parameters extracted from the result data (say by the parameter extractor), is used for classifying 620 the new assay, as described in further detail hereinbelow.

Optionally, the second exemplary method is implemented on an apparatus (say apparatus 4000) coupled itself to the chemical reaction apparatus in which the new assay is carried out, as described in further detail hereinbelow.

For example, apparatus 4000 may be implemented on a chip installed on the chemical reaction apparatus, say as a part of a controller connected to sensors inside a chemical reaction chamber, which forms a part of the chemical reaction apparatus, as described in further detail hereinbelow.

Reference is now made to FIG. 7A, which is a simplified flowchart illustrating a third method for remote chemical assay classification, according to an exemplary embodiment of the present invention.

A third exemplary method, according to an exemplary embodiment of the present invention may be implemented using electric circuits, computer instructions, etc.

The third exemplary method includes steps that a computer is programmed to perform.

Optionally, the third exemplary method is implemented on a computer server in remote communication with one or more dedicated client programs installed on remote computers (say on remote laboratory computers), as described in further detail hereinbelow.

In the third exemplary method, a plurality of parameter are extracted 710 from chemical reaction assay result data, say from QF-PCR graphs of the test assays, as described in further detail hereinabove. Each one of the test assays is characterized by a set of parameters extracted 710 from a respective one of the QF-PCR graphs.

Then, a dimensionality reduction technique such as Diffusion Mapping, is used to represent 720 the sets of parameters (and hence the test assays), as points in an embedded space (i.e. in a dimensionally reduced space), as described in further detail hereinbelow.

Further in the third exemplary method, there are extracted 730 intermediate products (say matrices) of the dimensionality reduction, usable for out-of-sample extension, say using Geometric Harmonics, as known in the art, and as described in further detail hereinbelow.

Then, a learning method such as SVM (Support Vector Machine) is used, to classify 740 the test assays, say by calculating a discriminant function which divides the points in the embedded space into two or more groups, as known in the art.

The discriminant function indicates for each of the points (and hence for the test assay represented by the point), the point's belonging to one of the groups, based on location of the point in the embedded space or on values of the parameters extracted for the test assay represented by the point.

Finally, data which defines an out-of-sample extension is packaged 750 in a specific file format, and sent to a remote computer.

The packaged 750 data which defines the out-of-sample extension, includes the discriminant function (say as a set of parameters).

The packaged 750 data further includes intermediate products of the dimensionality reduction technique, say matrices calculated during the diffusion mapping used for representing 720 the test assays in the embedded space.

Consequently, the remote computer may use the packaged 750 data, for classifying a new assay, as described in further detail hereinabove.

Reference is now made to FIG. 7B, which is a simplified flowchart illustrating a fourth method for remote chemical assay classification, according to an exemplary embodiment of the present invention.

A fourth exemplary method, according to an exemplary embodiment of the present invention may be implemented using electric circuits, computer instructions, etc.

The fourth exemplary method includes steps that a computer is programmed to perform.

According to an exemplary embodiment of the present invention Diffusion Mapping is used to represent 720 the sets of parameters (and hence the test assays), as points in an embedded space (i.e. in a dimensionally reduced space).

The embedded space enhances proximity among points representative of assays of qualitatively identical chemical reactions (say assays that are positive with respect to participation of a certain compound in the chemical reaction).

In one example, there are received 7010 sets of parameters extracted from result data of chemical reaction test assays, say as an input matrix of d columns and n lines. The input matrix contains n sets of d parameters.

Next, there is calculated 7020 an isotropic kernel, represented as a matrix of n columns and n lines. Each element in the matrix indicates if respective two of the sets of parameters are neighbors.

In one example, two sets of parameters are deemed neighboring, if the Euclidian distance between the two sets is no more than a maximal Euclidian distance, as preset by a user of the apparatus 3000, as known in the art.

That is to say that the isotropic kernel defines affinities between the sets of the parameters, which are derived from Euclidian distances among the received 7010 sets, as known in the art.

Next, there are calculated 7030 sizes (also referred to as degrees) of neighborhood for each one of the sets of parameters, say the number of sets within the preset maximal Euclidian distance from the set.

The calculated 7020 kernel is normalized, using the calculated 7030 sizes, say by dividing each element in the kernel by the size of the element's neighborhood. By normalizing the kernel, there is calculated 7040 a diffusion operator, represented as a matrix of n columns and n lines.

The diffusion operator represents the probability of a direct transition between two neighboring ones of the sets. The transition is a single step transition between two neighboring ones of the sets, in a Euclidian space in which the sets may be represented as points.

Next, there are calculated 7050 eigenvalues and corresponding eigenvectors, for the diffusion operator, say using Singular Value Decomposition, as known in the art. Consequently, there is provided a decomposition of the calculated 7020 isotropic kernel into eigenvalues and eigenvectors, as known in the art.

Each eigenvector has a corresponding eigenvalue, and the eigenvectors are ordered by decreasing values of their corresponding eigenvalues.

Then, a diffusion map is calculated 7060, using a number of highest ones of the calculated 7050 eigenvectors (i.e. eigenvectors which have the highest eigenvalues), say a number selected by a user of apparatus 3000.

Using the highest eigenvectors, there are provided coordinate values for each of the received 7010 sets of parameters, in a thus calculated embedded space which, unlike the Euclidian space, enhances proximity among points of higher affinity (i.e. points that represent the qualitatively identical chemical reaction assays).

Each of the eigenvectors used has n elements, one for each set of parameters. Each element in the eigenvector sets a single coordinate value for a point, which represents one of the received 7010 sets of parameters. The dimensionality of the calculated embedded space is determined by the number of eigenvectors used.

The resultant diffusion map includes the coordinate values set for each of the points in the calculated embedded space which enhances proximity among points representative of qualitatively identical chemical reactions.

The calculated 7060 diffusion map is used to construct 7070 a conversion function, which defines the calculated embedded space. That is to say that the conversion function is based, at least on each of the point's coordinate values, as included in the diffusion map (i.e. in the embedded space).

The conversion function's diffusion map is used to position 7080 the points in the calculated embedded space, thus representing each of the received 7010 sets of parameters (and thus the chemical reaction test assays), in the embedded space.

The fourth method further includes extracting an out-of-sample extension.

More specifically, the conversion function may include an out-of-sample extension method, usable for representing a new set of parameters in the embedded space. The out of sample extension method may be based on Geometric Harmonics, as known in the art. The out of sample extension methods provides coordinate values, for the new point.

Reference is now made to FIG. 8, which is a block diagram schematically illustrating a system for remote chemical assay classification, according to an exemplary embodiment of the present invention.

A system according to an exemplary embodiment of the present invention includes a chemical reaction apparatus 8000.

Optionally, the chemical reaction apparatus 8000 includes a reaction chamber 810, where a chemical reaction (say PCR) assay is performed.

Optionally, the chemical reaction apparatus 8000 further includes one or more sensors 830, for measuring values of a physical property of the chemical reaction.

For example, the sensors 830 may be photometric sensors installed in proximity of the reaction chamber 810. The photometric sensors measure intensity of to light emitted from the reaction chamber 810, as the chemical reactions assay progresses.

The photometric sensors measure the emission of light from the reaction chamber, using standard fluorescence methods, as known in the art.

The chemical reaction apparatus 8000 may further include a cycle counter 835, connected to the sensors 830. The cycle counter 835 instructs the sensors 830 to take measurement of the physical property, say once in an interval of time. Optionally, the interval of time is predefined by a user, as known in the art.

The chemical reaction apparatus 8000 may further include an Analog-to-Digital (A2D) converter 840, connected to the sensors 830. The Analog-to-Digital (A2D) converter 840 converts the measured values of the physical property of the chemical reaction into a digital format.

The System of FIG. 8 further includes a data accumulator 870, in communication with the A2D converter 840.

The data accumulator 870 receives the measured values from the A2D converter 840, and stores the measured values.

The data accumulator 870 may include, but is not limited to a CD-ROM, a Flash Memory, a RAM (Random Access Memory), etc., as known in the art.

The system may further include an apparatus 9000, implemented on a computer processor coupled to the chemical reaction apparatus 8000, through the data accumulator 870.

Apparatus 9000 may be implemented using electric circuits, computer instructions, etc. The apparatus 9000 may be implemented on a dedicated computer, on a computer chip connected to the chemical reaction apparatus 8000 or installed thereon, on a computerized controller connected to the chemical reaction apparatus 8000 or installed thereon, etc.

Optionally, the chemical reaction is a Polymerase Chain Reaction (PCR), say to a Quantitative Fluorescent Polymerase Chain Reaction (QF-PCR), as described in further detail hereinabove.

Apparatus 9000 includes an out-of-sample data receiver 910.

The out-of-sample data receiver 910 receives data which defines an out-of-sample extension, as described in further detail hereinbelow.

The out-of-sample extension is extracted on a remote computer (say on a server used by a company which provides classification services to laboratories), as described in further detail hereinabove.

The out-of-sample extension is extracted from classifying test assays of the chemical reaction, on the remote computer, into at least two groups, say using learning techniques and dimensionality reduction techniques, as described in further detail hereinbelow.

Optionally, the classification of the test assays on the remote computer is based on a non-linear technique such as diffusion mapping. The data which defines the extracted out-of-sample extension may include intermediary products of the non-linear technique, say matrices of the diffusion mapping, as described in further detail hereinbelow.

Optionally, the classification of the test assays on the remote computer is based on diffusion mapping and SVM. The data which defines the extension, may consist of intermediate products (say matrices) of the diffusion mapping technique and an SVM discriminant function, as described in further detail hereinbelow.

The apparatus 9000 further includes a new assay classifier 920, in communication with the out-of-sample data receiver 910.

The new assay classifier 920 classifies the assay of the chemical reaction preformed in the chamber 810 (i.e. a new assay of the chemical reaction), into one of the groups that the test assays are classified into, using the data which defines the out-of-sample extension, as described in further detail hereinbelow.

The apparatus 9000 further includes a parameter extractor 930, in communication with the new assay classifier 920.

The parameter extractor 930 extracts one or more parameters from result data of the new assay performed in the chamber 810, and the new assay classifier 920 uses the extracted parameters, for classifying the new assay, as described in further detail hereinbelow.

The apparatus 9000 further includes a result data receiver 940, in communication with the parameter extractor 930.

The result data receiver 940 receives result data (say the fluorescence intensity values measured by the sensors 830 during the new chemical reaction assay) of the new assay, from the data accumulator 870, and forwards the result data to the parameter extractor 930.

The new assay classifier 920 classifies the new assay of the chemical reaction into one of the groups that the test assays are classified into, using the data which defines the out-of-sample extension, and the parameters extracted by the parameter extractor 930, as described in further detail hereinbelow.

The apparatus 9000 further includes a display 990, such as a small LCD screen or a set of small LED lights, in communication with the new assay classifier 920.

Upon successful classification of the new assay, the new assay classifier 920 uses the display, to convey the classification's result to a user.

For example, the new assay classifier 920 may convey the classification's result to the user, by turning on one of the LED lights (say a red light which may indicate a negative assay), or by presenting a message (say a 'Negative Assay' message) on the small LCD screen.

Out-of-Sample Extensions for Dimensionality Reduction Techniques

Real-world data, such as the chemical reaction assays of the present invention, usually has a high dimensionality. That is to say that the real world data may need to be characterized by many parameters.

In order to handle such real-world data adequately, the dimensionality of the real-world data may needs to be reduced.

Dimensionality reduction is a transformation of high-dimensional data into a meaningful representation of reduced dimensionality (say the embedded space), as described in further detail hereinabove.

Dimensionality reduction is important in many domains, since it may mitigate computational complexity inflicted by high dimensionality and other undesired properties of high-dimensionality spaces.

Ideally, the reduced representation has a dimensionality that corresponds to to the real-world data's intrinsic dimensionality. The intrinsic dimensionality of the real-world data is a minimum number of parameters needed to account for observed properties of the real-world data.

As a result, dimensionality reduction facilitates, among others, classification, visualization, and compression of high-dimensional data.

Traditional dimensionality reduction is performed using linear techniques such as Principal Components Analysis (PCA), factor analysis, and classical scaling.

However, the linear techniques cannot adequately handle complex nonlinear data.

By contrast, nonlinear dimensionality techniques have an ability to deal with complex nonlinear data.

In particular for real-world data, nonlinear dimensionality reduction techniques may offer an advantage, because real-world data is likely to form a highly nonlinear manifold, when presented in a regular Euclidian space.

The dimensionality reduction techniques, as well as other methods used for classifying the test assays of the present invention, require extensive computational resources, typically found on strong computer servers used by big laboratories and academic institutions.

In particular, when a new assay needs be classified, a completely accurate classification requires a complete re-calculation of the whole embedded space, by applying the dimensionality reduction techniques on results of both the test assays and the new assay.

According to an exemplary embodiment of the present invention, an out-of-sample extension is extracted from the classification of the test assays, on the central server.

The out-of-sample extension is a method for classifying a new assay into one of the groups (say the negative and positive groups) resultant upon the classification of the test assays.

The out-of-sample extension classifies the new assay without a complete re-calculation of the whole embedded space, say using intermediate products of the classification of the test assay.

More specifically, the out-of-sample extension may represent the new assay in a point in the (original) embedded space, using matrices created during dimensionality reduction based calculation of the embedded space, without a computationally heavy re-calculation of the embedded space, based on parameters extracted from both the new assay and the test assays.

While, the out-of-sample extension is computationally simpler than the techniques used for classifying the test assays, the out-of-sample extension involves a tolerable loss in accuracy of classification.

Out-of-sample extensions are available for a number of dimensionality reduction techniques.

The Out-of-sample extensions may be subdivided into parametric and nonparametric out-of-sample extensions.

In a parametric out-of-sample extension, the dimensionality reduction technique provides all parameters that are necessary in order to transform new data from a high-dimensional representation (say a Euclidian space) into a low-dimensional representation.

For example, in linear techniques such as PCA (Principal component analysis), the transformation is defined using linear mapping applied on original data (i.e. test assays), also referred to as 'training data', for classifying the original data, as known in the art.

For auto-encoders such as Neuronal Networks, a trained network defines the transformation from the high-dimensional representation to the low-dimensional representation.

For non-linear dimensionality reduction techniques, a parametric out-of-sample extension is not available, and therefore, a nonparametric out-of-sample extension is required.

Nonparametric out-of-sample extensions perform an estimation of the transformation from the high-dimensional to the low-dimensional space. Typically, the non-parametric out-of-sample extensions are based on intermediate products of the dimensionality reduction technique.

There are many currently used out-of-sample extensions for non-linear dimensionality reduction techniques.

For instance, Nystrom approximation is an out-of-sample extension of choice for Kernel PCA, as known in the art.

J. C. Plat defines an exemplary Nystrom approximation based out-of-sample extension in "FastMap, MetricMap, and Landmark MDS, are all Nystrom algorithms", In Proceedings of the $10^{th}$ International Workshop on Artificial Intelligence and Statistics, pages 261-268, 2005.

Nystrom approximation is also used for out-of-sample extension, for the Isomap, LLE, and Laplacian Eigenmaps techniques.

Y. Bengio defines an exemplary Nystrom approximation based out-of-sample extensions for LLE and Laplacian Eigenmaps, in an article entitled "Out-of-sample extensions or LLE, Isomap, MDS, eigenmaps, and spectral clustering", in Advances in Neural Information Processing Systems, volume 16, Cambridge, Mass., USA, 2004, in The MIT Press.

Nystrom approximation can be used for Isomap too, as known in the art.

H. Choi and S. Choi describe an exemplary Nystrom approximation based out-of-sample extension for Isomap, in an article entitled "Robust kernel Isomap", in Recognition, 40(3):853-862, 2007.

Similarly, V. de Silva and J. B. Tenenbaum, describe an exemplary Nystrom approximation based out-of-sample extensions for Isomap, in "Global versus local methods in nonlinear dimensionality reduction" published in Advances in Neural Information Processing Systems, volume 15, pages 721-728, Cambridge, Mass., USA, 2003. The MIT Press.

Among several known in the art out-of-sample extensions for MVU (Maximum Variance Unfolding):

Computing a linear transformation from a set of landmark points to a complete dataset of test data, as illustrated by K. Q. Weinberger, B. D. Packer, and L. K. Saul in "Nonlinear dimensionality reduction by semi-definite programming and kernel matrix factorization". The Proceedings of the 10th International Workshop on AI and Statistics, Barbados, Wis., 2005. The Society for Artificial Intelligence and Statistics.

Finding a linear transformation by computing eigenvectors that correspond to a laplacian graph's smallest eigenvalues, as illustrated by K. Q. Weinberger, F. Sha, Q. Zhu, and L. K. Saul in an article entitled "Graph Laplacian regularization for large-scale semidefinite programming", in Advances in Neural Information Processing Systems, volume 19, 2007.

Approximating a kernel's eigenfunction using Gaussian basis functions, as illustrated by T. J. Chin and D. Suter, in an article entitled "Out-of-sample extrapolation of learned manifolds", in IEEE Transactions on Pattern Analysis and Machine Intelligence, 30(9):1547-1556, 2008.

A nonparametric out-of-sample extension that may be applied to many nonlinear dimensionality reduction technique, is proposed by Teng et at al, in an article entitled "Supervised learning on local tangent space", in Lecture Notes on Computer Science, volume 3496, pages 546-551, Berlin, Germany, 2005. Springer Verlag.

Teng finds the nearest neighbor of a new data-point in a high-dimensional representation, and computes the linear mapping from the nearest neighbor to a corresponding low-dimensional representation. The low-dimensional representation of the new data-point is found by applying the same linear mapping to the new data-point.

A method of choice for calculating an out-of-sample extension, for Diffusion Mapping, is Geomatric Harmonics.

Geometric Harmonics and its employment in diffusion mapping is described by S. Lafon, Y. Keller, R. R. Coifman in "Data fusion and multicue data matching by diffusion maps", IEEE Trans. Pattern Anal. Machine Intell., 28(11), pp. 1784-1797, 2006, and by R. R. Coifman and S. Lafon, in "Geometric harmonics", Appl. Comput. Hannon. Anal., 21, pp. 31-52, July 2006.

An exemplary Geomatric Harmonics based out-of-sample extension for Diffusion Mapping is given by Genussov, Lavner, and Cohen, in "Classification of Unvoiced Fricative Phonemes using Geometric Methods", Proc. 12th International Workshop on Acoustic Echo and Noise Control, IWAENC-2010, Tel-Aviv, Israel, Aug. 30-Sep. 2, 2010.

General Further Discussion

An exemplary embodiment of the present invention describes creation of a small portable file that represents a cache of pre-calculated methods and parameters. The cache may be used to classify new samples, while utilizing only small memory to footprint and minimal computing resources.

This provides for real-time classification of new test assays of a chemical reaction, even when the classification model used for classifying, is based on complicated classification and embedding algorithms applied on large data-sets of test assays of the chemical reaction, as described in further detail hereinabove.

Creation of a Classification Transportable Medium (D)

1. Numerical features are extracted from chemical curves of a training set
   1.1. Each curve is now represented by a set of numbers
2. Optionally, dimensionally reduction or an embedding technique is used to represent the sample in a space with a reduced number of dimensions, that optionally also enhances group separation
   2.1. A list of parameters is extracted from the calculation of the embedded space, and stored (A). The parameters are required to perform an out of sample calculation of new samples into that embedded space.
3. Optionally, a classification method is used on the data set, to create a discriminant function that separates the data into a number of groups, based in its numerical features or its location in the embedded space
   3.1. The parameters of the discriminant function are extracted, and stored (B)
4. The out-of-sample method (A) and the discriminant function (B) are stored, and a file (or files or database) that stores them (D) is preserved to be used for later classification, which is the transportable medium for classification An Out-of-Sample Classifier Computer Program (E)

The out of sample classifier is a computer program that:
1. Extracts numerical features (i) from new chemical curves of data that is to be classified, quantified or measured for being an outlier.
2. If a dimensionality reduction out of sample method (A) is created, numerical features are fed into an out-of-sample method (G) compatible with the embedding method, while utilizing parameter data (A), in order to create out-of-sample embedded coordinates (H).
3. If a dimensionality reduction out of sample method (A) and a classifier function (B) are created, embedded coordinates are fed into the discriminant function stored (B), to achieve classification.
4. If only a classifier function (B) is created, extracted numerical features are fed into the discriminant function (B), to achieve classification.

An Out-of-Sample Classifier Device (J)

1. The computer program (E) is stored on a computer, an embedded device, a chip or another computing device (J)
2. The transportable medium (D) is inserted as an external attachable memory module, or sent by computer communications (emails etc.) to the computing device.
3. On arrival of new reaction parameters, the device (J) performs program (E), using parameters stored in the transportable medium (D), to perform embedding and classification on the new reaction parameters.
4. Results are sent back to the caller or operator, or logged in the device for later analysis An Out of Sample Classifier Compute-Cloud Node (L)

1. The computer program (E) is stored in an inactive Operating System image, along with control instructions.
2. On demand, the computer program is loaded into a server, and is run as a virtualized server instance (M), as known in the art.
3. The file (D) is sent to instance (M), so that (M) is now able to classify validate and quantify new samples.
4. New samples are sent to instance (M), and are classified. The results are sent back the caller, or stored in cloud file storage or a cloud database.
5. The server instance can be discarded after use, as no state information needs to be saved on it (Stateless).

Out of Sample Software as a Service (SaaS)

1. The computer program (E) is stored in a computer or a virtualized server.
2. File (D) is stored along with program (E), or sent to program (E) upon execution of the SaaS module.
3. On arrival of new reaction parameters, device (SaaS) runs programs (E) using parameters stored in file (D) to perform classification, validation as outlier and quantification on the new reaction parameters.
4. Results are sent back to the caller or operator, or logged in a database.

Creation of the Transportable Medium (D)

A Diffusion Mapping Example

1. A list of curves is input, along with control samples, which are routinely used when using chemo-metrics and specifically PCR.
2. Features of the reaction curve, such as elbow points, maximal value, etc., are extracted from curves.
3. A dimensionality reduction embedding technique such as Diffusion mapping, or another technique which enhances proximity among curves exhibiting similar features, is applied on the extracted features.
4. Intermediate matrix data is preserved from the embedding techniques, as required by the out-of-sample method of choice. Then stored for later use.
5. For diffusion maps, the out-of-sample method of choice is Geometric Harmonics.
6. Geometric Harmonics is a part of Phd. Lafon Dissertation: *Diffusion maps and geometric harmonics*, see in: http://www.cims.nyu.edu/~gunturk/Seminar_Data/Lafon_abstract.html
7. Support-Vector-Machine algorithm is used to create a discriminant function, using the input control samples.
   7.1. The discriminant function and its parameters are preserved and stored for later use
8. A quantification method is used to quantify samples based on the original set, such as using a Dilution Series to quantify samples by.
   8.1. The parameters and method of quantification (i.e. the values of the dilution series line of best fit) are saved.
9. An outlier detection method may also be used to create a function that validates a point to be an outlier by its numerical features.
   9.1. The outlier boundaries or validation function are saved.
10. All saved data is joined in a file (D).

Out-of-Sample Classifier Program (E)

A Diffusion Mapping Example

1. A computer program is made that, when input a file (D):
   1.1. Extracts numerical features from a list of points.
   1.2. Runs the Geometric Harmonics method with the parameters in file (D), to embed the input points.
   1.3. Send results back to caller.

It is expected that during the life of this patent many relevant devices and systems will be developed and the scope of the terms herein, particularly of the terms "Computer", "Modem", "Computer Network Card", "Chip", "USB Memory", "SD Memory", and "Smart Card", is intended to include all such new technologies a priori.

It is appreciated that certain features of the invention, which are, for clarity, described in the context of separate embodiments, may also be provided in combination in a single embodiment.

Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

In addition, citation or identification of any reference in this application shall not be construed as an admission that such reference is available as prior art to the to present invention.

What is claimed is:

1. A system for remote chemical assay, the system comprising:
    a computer processor;
    a chemical reaction apparatus comprising at least one sensor configured to make at least one measurement during an assay of a chemical reaction taking place on the chemical reaction apparatus;
    a data receiver, configured to receive data usable for classifying the assay of the chemical reaction and based on results of a plurality of assays of the chemical reaction, from a remote computer; and
    an assay classifier, implemented on said computer processor, in communication with said data receiver and chemical reaction apparatus, configured to classify the assay of the chemical reaction, using the received data usable for classifying the assay and result data based on the measurement made during the assay of the chemical reaction.

2. The system of claim 1, further comprising a result data receiver, configured to receive the result data based on the measurement made during the assay of the chemical reaction.

3. The system of claim 1, further comprising a parameter extractor, configured to extract at least one parameter from a plurality of values measured during the chemical reaction assay on the chemical reaction apparatus, wherein said assay classifier is further configured to use the extracted parameter, for classifying the assay.

4. The system of claim 1, wherein said chemical reaction apparatus further comprises a reaction chamber in which the chemical reaction takes place.

5. The system of claim 1, wherein said chemical reaction apparatus further comprises an analog to digital converter, configured to receive a plurality of values measured on the chemical reaction apparatus during the assay, and convert the received measured values into a digital format.

6. The system of claim 1, further comprising a data accumulator, configured to receive and accumulate result data based on the measurement made during the assay of the chemical reaction on the chemical reaction apparatus, wherein said assay classifier is further configured to use the accumulated result data, for classifying the assay.

7. The system of claim 6, wherein said assay classifier is coupled to said chemical reaction apparatus by said data accumulator.

8. The system of claim 1, further comprising a data communicator, configured to communicate with the remote computer over a cellular network, for receiving the data usable for classifying the assay, and forward the received data usable for classifying the assay, to said data receiver.

9. The system of claim 1, further comprising a data communicator, configured to communicate with the remote computer over the internet, for receiving the data usable for classifying the assay, and forward the received data usable for classifying the assay, to said data receiver.

10. The system of claim 1, wherein said computer processor is installed on the chemical reaction apparatus.

11. The system of claim 1, wherein said computer processor is installed on a controller connected to sensors inside a reaction chamber forming a part of the chemical reaction apparatus.

12. A system for chemical reaction and data accumulation, the system comprising:
    a chemical reaction apparatus comprising at least one sensor configured to make at least one measurement during a chemical reaction taking place on said chemical reaction apparatus; and
    a data accumulator, associated with said chemical reaction apparatus, configured to receive and accumulate result data based on the measurement made during the chemical reaction, and to couple said chemical reaction apparatus to a computer.

13. The system of claim 12, wherein said data accumulator is implemented on a chip installed on the chemical reaction apparatus.

14. The system of claim 12, wherein said data accumulator is a part of a controller connected to a sensor inside a chemical reaction chamber forming a part of said chemical reaction apparatus.

15. The system of claim 1, wherein the data is further based on a plurality of parameters extracted from reaction graphs of the plurality of assays of the chemical reaction.

* * * * *